United States Patent
Schuetz

[19]

[11] Patent Number: 5,843,090
[45] Date of Patent: Dec. 1, 1998

[54] STENT DELIVERY DEVICE

[75] Inventor: Wallace J. Schuetz, Eden Prairie, Minn.

[73] Assignee: Schneider (USA) Inc., Plymouth, Minn.

[21] Appl. No.: 743,204

[22] Filed: Nov. 5, 1996

[51] Int. Cl.⁶ .................................................. A61F 11/00
[52] U.S. Cl. ......................... 606/108; 606/192; 606/195; 606/198
[58] Field of Search .................................. 606/108, 198, 606/195, 194, 192; 623/12; 604/96

[56] References Cited

U.S. PATENT DOCUMENTS

| | | |
|---|---|---|
| 4,655,771 | 4/1987 | Wallsten . |
| 4,848,343 | 7/1989 | Wallsten et al. . |
| 4,886,062 | 12/1989 | Wiktor ..................................... 606/195 |
| 4,950,227 | 8/1990 | Savin et al. .............................. 606/192 |
| 4,954,126 | 9/1990 | Wallsten . |
| 4,990,151 | 2/1991 | Wallsten . |
| 5,026,377 | 6/1991 | Burton et al. ........................... 606/108 |
| 5,061,275 | 10/1991 | Wallsten et al. . |
| 5,071,407 | 12/1991 | Termin et al. . |
| 5,201,757 | 4/1993 | Heyn et al. ............................. 606/198 |
| 5,266,073 | 11/1993 | Wall . |
| 5,464,408 | 11/1995 | Duc ........................................ 606/108 |
| 5,476,476 | 12/1995 | Hillstead . |
| 5,484,444 | 1/1996 | Brannschweiler ...................... 606/108 |
| 5,534,007 | 7/1996 | St. Germain et al. ................. 606/108 |
| 5,571,135 | 11/1996 | Fraser et al. ........................... 606/198 |
| 5,591,172 | 1/1997 | Bachmann et al. .................... 606/108 |
| 5,603,698 | 2/1997 | Roberts et al. ......................... 606/198 |
| 5,628,754 | 5/1997 | Shevlin et al. .......................... 606/108 |
| 5,628,755 | 5/1997 | Heller et al. ............................ 606/108 |
| 5,634,928 | 6/1997 | Fischell et al. ........................ 606/108 |
| 5,645,559 | 7/1997 | Hachtman et al. ..................... 606/198 |
| 5,653,689 | 8/1997 | Buelna et al. ........................... 606/108 |
| 5,658,311 | 8/1997 | Baden ..................................... 606/192 |
| 5,662,703 | 9/1997 | Yurek et al. ............................... 623/1 |
| 5,690,644 | 11/1997 | Yurek et al. ........................... 606/106 |
| 5,695,499 | 12/1997 | Helgerson et al. .................... 606/108 |
| 5,709,703 | 1/1998 | Lukic et al. ............................ 606/198 |
| 5,743,874 | 4/1998 | Fischell et al. ........................... 604/96 |

FOREIGN PATENT DOCUMENTS

| | | |
|---|---|---|
| 0699451A2 | 3/1996 | European Pat. Off. . |
| 0720837A1 | 7/1996 | European Pat. Off. . |
| WO 94/24961 | 11/1994 | WIPO . |
| WO 95/26777 | 10/1995 | WIPO . |

OTHER PUBLICATIONS

European Search Report, 16 Feb. 1998, for appl. No. 973078033–2305.

*Primary Examiner*—Richard J. Apley
*Assistant Examiner*—Justine R. Yu
*Attorney, Agent, or Firm*—Faegre & Benson LLP

[57] ABSTRACT

A balloon catheter with a stent delivery device having inner and outer catheters, with the outer catheter having a second lumen for inflation of the balloon. The delivery device also includes a radiopaque marker band adjacent each end of the stent located at the distal end of the device adjacent a tapered tip. The device also includes a manifold having a flushing port fluidly coupled to an annular space between the inner and outer catheters and an inflation port fluidly coupled to the second lumen of the outer catheter for inflating the balloon.

15 Claims, 5 Drawing Sheets

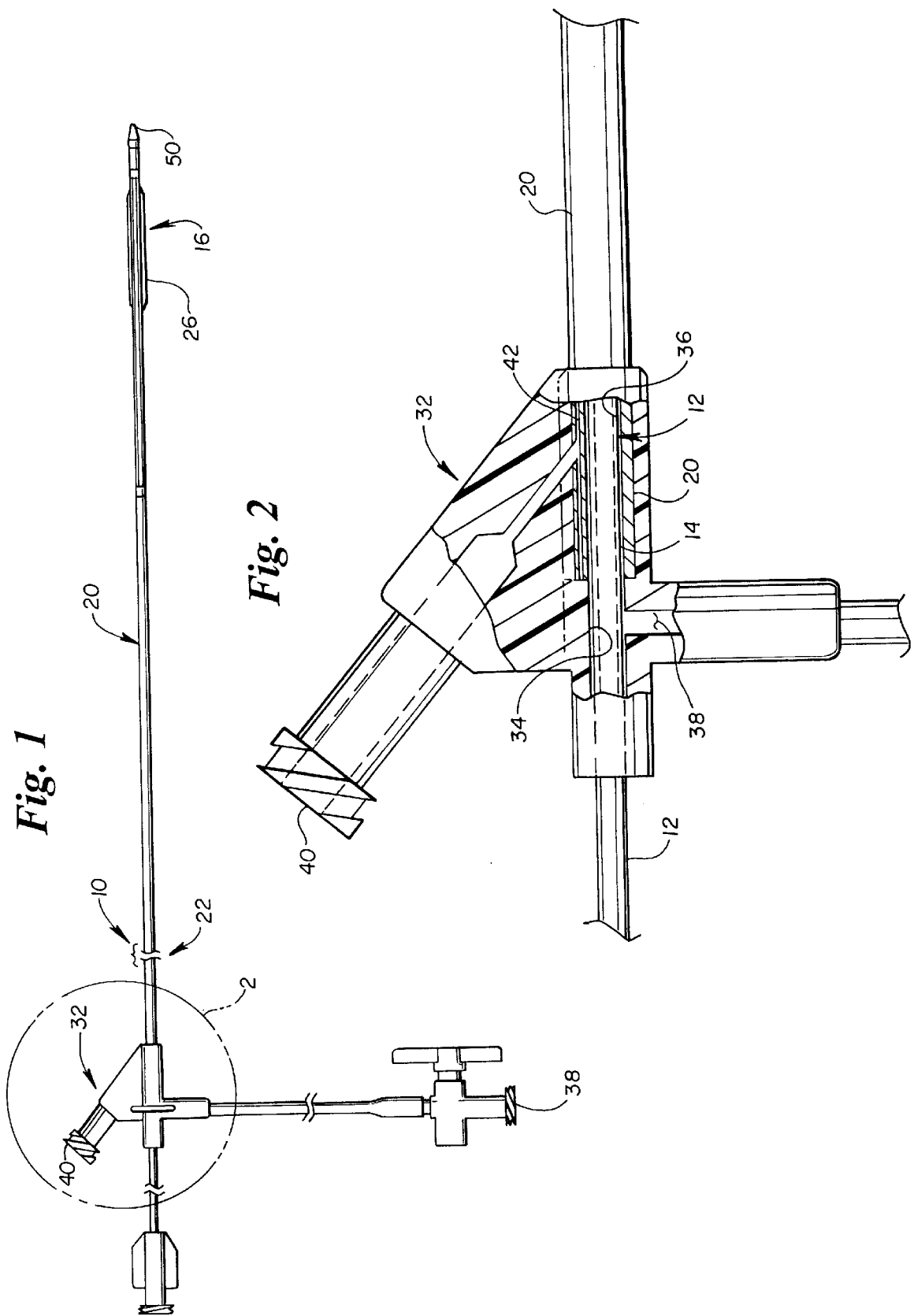

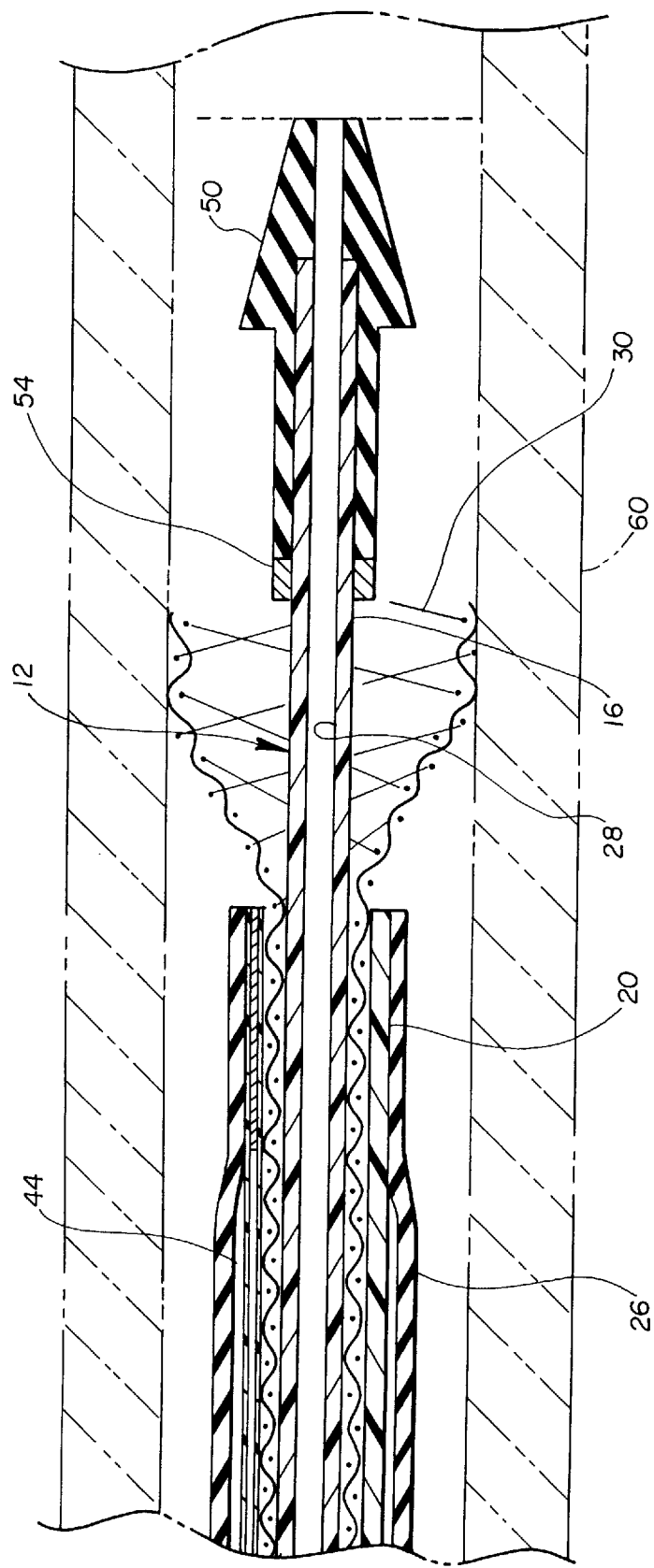

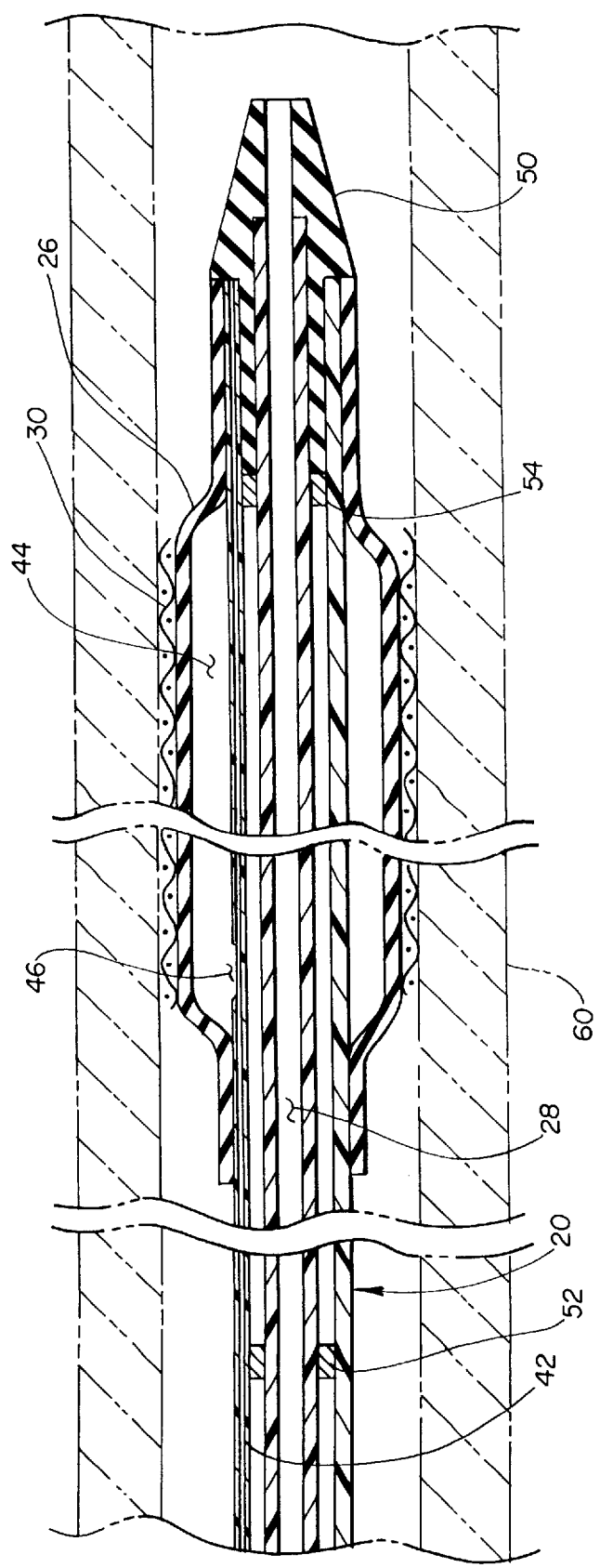

STENT DELIVERY DEVICE

BACKGROUND OF THE INVENTION

The present invention relates to a delivery system for delivering and deploying a stent to a treatment site within a vessel of the body of a living animal or living human. The delivery system of this invention includes a balloon catheter for dilating the vessel before deploying the stent and also after deploying the stent, if desired, without complete removal and insertion of separate catheters as was typically required in the prior art.

BRIEF DESCRIPTION OF THE DRAWINGS

FIG. 1 is an overall view of a stent delivery apparatus useful in the practice of the present invention.

FIG. 2 is an enlarged view partly in section of detail 2 of FIG. 1.

FIG. 6 is a view similar to FIG. 3, but with the outer catheter partially retracted and the stent partially deployed.

FIG. 7 is a view similar to that of FIG. 3, but with the stent fully deployed and with the outer catheter returned to the position shown in FIG. 3 and with the balloon inflated in post-deployment dilation.

DETAILED DESCRIPTION OF THE INVENTION

Figure 3:
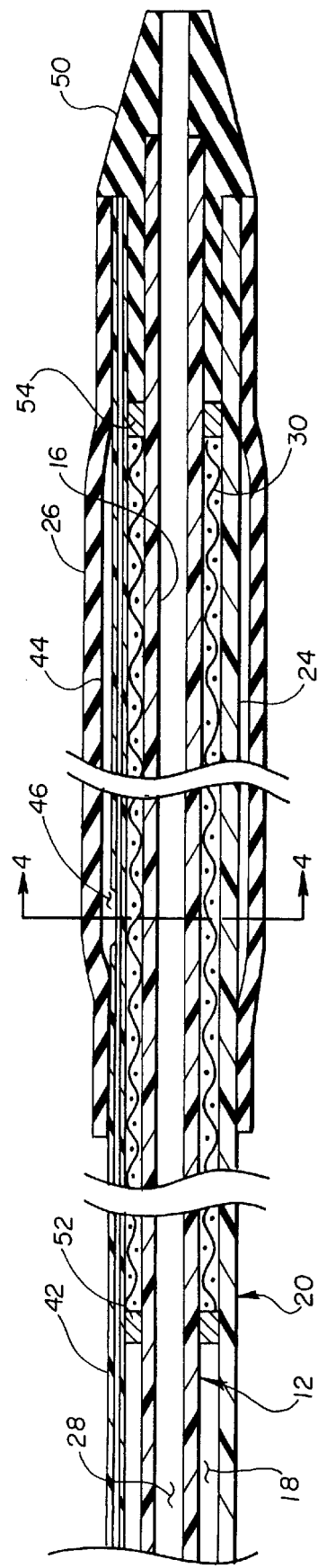
FIG. 3 is a section view of a distal end of the apparatus of FIG. 1 showing inner and outer catheters, a stent in a radially inwardly collapsed condition and a balloon carried on the apparatus and in a deflated condition.

Referring to the Figures and most particularly to FIGS. 1, 2, and 3, a stent delivery system or medical device 10 may be seen. System or device 10 includes an inner catheter 12 having a proximal portion 14 and a distal portion 16. System 10 further has an outer catheter 20 having a proximal portion 22 and a distal portion 24. The outer catheter 20 is disposed about the inner catheter 12 and forms an annular space 18 between at least the distal portions 16 and 24 of the inner and outer catheters 12, 20. Device 10 also has a dilation balloon 26 disposed about and secured by conventional means to the distal portion 24 of the outer catheter, and device 10 further has a stent 30 disposed in the annular space 18 between the distal portion 24 of the outer catheter 20 and the distal portion 16 of the inner catheter 12.

Figure 4:
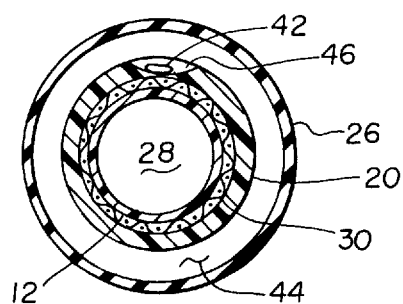
FIG. 4 is a section view taken along line 4—4 of FIG. 3.
Figure 5:
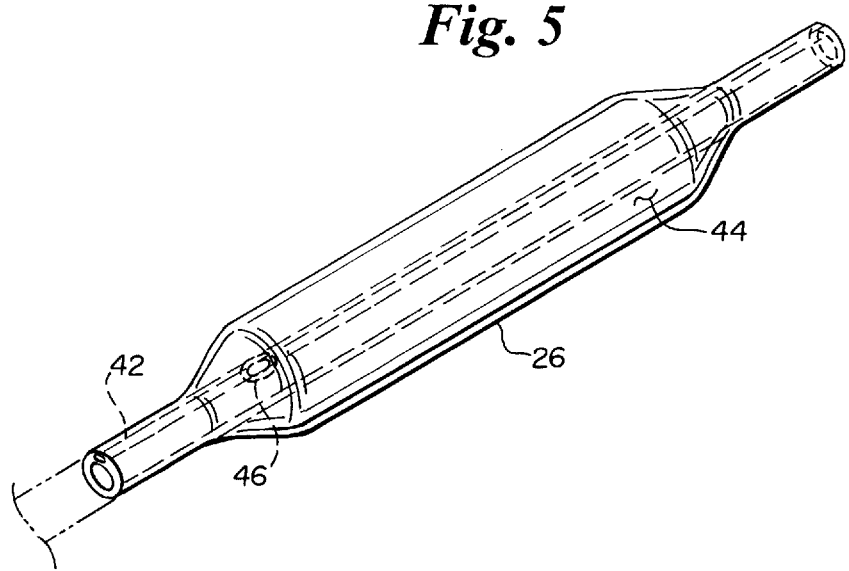
FIG. 5 is a perspective view of a portion of the apparatus of FIG. 3, but with the balloon inflated.

Device 10 also has a valve body or manifold 32 secured (by conventional means) to the outer catheter 20. Manifold 32 has a through lumen 34 aligned with the through lumen 36 of outer catheter 20. Inner catheter 12 is received in lumen 36. A flushing port 38 is formed as part of manifold 32 and is in fluid communication with lumen 34, and annular space 18 when inner catheter is received in device 10. The flushing port 38 may be used to introduce a flushing or hydrophilic-coating-activating liquid (such as a saline solution), or to introduce a conventional lubricating liquid into the annular space 18 if desired. The flushing fluid is useful to eliminate air in the annular space 18, reducing the chance of air emboli therein. Valve body 32 also preferably has an inflation port 40 in fluid communication with a auxiliary or second lumen 42 of outer catheter 20. Referring now also to FIGS. 4 and 5, auxiliary or second lumen 42 is fluidly coupled to an inflation plenum 44 between balloon 26 and outer catheter 20 via a skive 46. A guide wire (not shown) may be inserted in lumen 34 of manifold 32 to extend into lumen 28 of inner catheter 12, and through a tip 50, as desired.

Tip 50 of system 10 is preferably made of a soft elastomeric material to provide a relatively streamlined leading surface for the stent delivery system to ease insertion into the vessel. A pair of radiopaque bands 52, 54 are preferably located at proximal and distal ends, respectively, of the stent as may be seen most clearly in FIG. 3. Bands 52 and 54 provide pronounced demarcation of the ends of stent 30 to aid in the radiographically assisted or directed placement of the stent 30 in a vessel 60 as, for example, shown in phantom in FIGS. 6 and 7. The balloon may be axially configured within bands 52 and 54 so that the bands provide an indication of the balloon location for the purpose of positioning the balloon at a desired dilatation site. In certain embodiments, a radiopaque band will define the proximal and/or distal end of the balloon.

The stent 30 of the delivery system 10 is preferably a self-expanding type carried in a collapsed condition between the inner catheter 12 and the outer catheter 20. U.S. Pat. No. 4,655,771 B1, as re-examined, for a PROSTHESIS COMPRISING AN EXPANSIBLE OR CONTRACTILE TUBULAR BODY, naming Hans I. Wallsten as inventor, is hereby expressly incorporated by reference as an example of such a self-expanding prosthesis or stent. Balloon 26 is preferably located directly radially outwardly of stent 30 exteriorly of outer catheter 20. In use, the device 10 is preferably maneuvered to position the distal portion 16 carrying stent 30 at a treatment site (typically using a radiographic techniques, either with or without bands 52 and 54) followed by inflating the balloon 26 to dilate the vessel 60 and thereafter deflating the balloon 26. The balloon 26 is inflated or pressurized (typically by injecting saline solution via inflation port 40) using the separate second lumen 42 in the outer catheter 20. Next the outer catheter 20 is retracted (after the balloon 26 is deflated by extracting the saline solution via port 40) while the position of the inner catheter 12 is maintained such that the stent 30 is deployed at the treatment site. Alternatively, the distal portion 16 may be positioned slightly distal of the treatment site to allow for slight proximal migration of the stent 30 during deployment. The inner catheter 12 preferably has a radially outwardly directed stop means or element (which in the embodiment shown is combined in function with radiopaque band 52) located adjacent a proximal end of the stent 30 to restrain axial movement of the stent 30 as the outer catheter 20 is retracted in deploying the stent 30. Finally, the device 10 is withdrawn from the vessel or canal 60 either with or without returning the outer catheter 20 distally towards tip 50. It is to be understood that pre-deployment inflation of balloon 26 may be omitted, if desired. Furthermore, outer catheter 20 may be moved to position balloon 26 radially interiorly of stent 30 and inflated after deployment of stent 30 as shown in FIG. 7, if desired. Balloon 26 is thereafter deflated and device 10 withdrawn from vessel 60.

It may thus be seen that the present invention includes a method of using the combined stent and delivery device to both dilate a partially occluded portion of a body canal and deploy a stent therein without the necessity of removing the device between those two operations where the operations include dilating a partial occluded portion of a body canal using a balloon carried on a distal portion of the device and the further operation of retracting an outer sleeve or catheter overlying a self-expanding stent such that the stent is released in the dilated portion of the body canal. According to one aspect of the method of the present invention, in certain procedures the distal region of the delivery device may be preferably located slightly distal of the treatment site prior to stent deployment so that the stent will be deployed at the desired location with respect to the treatment site. This will allow for the known propensity of certain self-expanding stents to migrate slightly proximally during deployment in certain situations.

More particularly, the method includes inserting the stent delivery device 10 into the vessel 60 wherein the device has a self-expanding stent 30 carried in a collapsed condition between the inner and outer catheters 12, 20 and restrained against proximal axial movement by a step or element 52 and the device 10 further has a dilation balloon 26 carried thereon, all at a distal region of the device 10. The method also includes manoeuvering the device 10 to position the stent 30 at a treatment site, typically a partially occluded portion of the vessel 60, whereupon the outer catheter 20 is retracted such that the stent 30 is deployed at the treatment site, and the device 10 is thereafter withdrawn from the vessel 60. Further aspects of the method of the present invention include the additional steps of positioning the balloon 26 at the treatment site, inflating the balloon 26 to dilate the vessel 60, and deflating the balloon 26, all after manoeuvering the device 10 to position the stent 30 at the treatment site and before deploying the stent 30. Still further (optional) aspects of the method of the present invention include the additional steps of advancing the outer catheter 20 distally to position the balloon 26 interiorly (or radially inwardly) of the stent 30 at the treatment site, inflating the balloon 26 within the stent 30 (to further expand or "set" the stent 30) and thereafter deflating the balloon 26, in this case all after deploying the stent 30 and before withdrawing the device 10 from the vessel 60. Of course, it is to be understood that both pre- and post-deployment balloon inflation or vessel dilation may be utilized in the practice of the present invention.

The invention is not to be taken as limited to all of the details thereof as modifications and variations thereof may be made without departing from the spirit or scope of the invention.

What is claimed is:

1. A medical device comprising:
    a) an inner catheter having a proximal portion and a distal portion;
    b) an outer catheter having a first lumen therethrough and a proximal portion and a distal portion, the outer catheter disposed around the inner catheter and forming an annular space between the distal portion of the outer catheter and the distal portion of the inner catheter;
    c) a dilation balloon disposed around the distal portion of the outer catheter; and
    d) a stent disposed in the annular space between the distal portion of the outer catheter and the distal portion of the inner catheter; and
    e) a manifold having
        i) a flushing port fluidly coupled to the annular space between the inner catheter and first lumen of the outer catheter, and
        ii) an inflation port fluidly coupled to a second lumen in the outer catheter to permit inflation of the balloon.

2. The device of claim 1 wherein the inner catheter further comprises a radially outwardly directed element adjacent a proximal end of the stent to restrain axial movement of the stent as the outer catheter is retracted.

3. The device of claim 2 wherein the element comprises a first radiopaque band.

4. The device of claim 3 further comprising a second radiopaque band adjacent a distal end of the stent.

5. The device of claim 1 wherein the stent is a self-expanding stent.

6. The device of claim 5 wherein the annular space between the inner and outer catheters is sized to retain the stent in a radially collapsed condition.

7. The device of claim 1 wherein the manifold further comprises:
    iii) a through lumen for permitting passage of a guide wire therethrough.

8. A stent delivery system comprising:
    a) an inner catheter having a proximal portion and a distal portion, the inner catheter forming a lumen at least in its distal portion;
    b) an outer catheter disposed around the inner catheter and forming an annular space between the inner and outer catheters, the outer catheter having a dilation balloon disposed around a distal region thereof, and a lumen fluidly coupled to the interior of the dilation balloon; and
    c) a stent located at a distal region of the annular space between the inner and outer catheters,
    wherein the balloon is positioned radially outwardly of the stent and further wherein the balloon is inflatable for pre-stent-deployment dilation of a vessel containing the device.

9. The stent delivery system of claim 8 wherein the inner catheter further comprises a tapered tip at an end of the distal portion thereof.

10. The stent delivery system of claim 8 wherein the stent is releasable from the annular space between the inner and outer catheters by retraction of the outer catheter away from the distal end of the inner catheter.

11. A medical device comprising:
    a) an inner catheter having a proximal portion and a distal portion;
    b) an outer catheter having a first lumen therethrough and a proximal portion and a distal portion, the outer catheter disposed around the inner catheter and forming an annular space between the distal portion of the outer catheter and the distal portion of the inner catheter;
    c) a dilation balloon disposed around the distal portion of the outer catheter; and
    d) a stent disposed in the annular space between the distal portion of the outer catheter and the distal portion of the inner catheter
    wherein the dilation balloon is positioned radially outwardly of the stent and further wherein the balloon is inflatable for pre-stent-deployment dilation of a vessel containing the device.

12. A stent delivery system comprising:
    a) an inner catheter having a proximal portion and a distal portion, the inner catheter forming a lumen at least in its distal portion;
    b) an outer catheter disposed around the inner catheter and forming an annular space between the inner and outer catheters, the outer catheter having a dilation balloon disposed around a distal region thereof, and a lumen fluidly coupled to the interior of the dilation balloon; and
    c) a stent located at a distal region of the annular space between the inner and outer catheters d) a manifold having
  i) a flushing port fluidly coupled to the annular space between the inner catheter and first lumen of the outer catheter, and
  ii) an inflation port fluidly coupled to a second lumen in the outer catheter to permit inflation of the balloon.

13. The stent delivery system of claim 12 wherein the inner catheter further comprises a tapered tip at an end of the distal portion thereof.

14. The stent delivery system of claim 12 wherein the stent is releasable from the annular space between the inner and outer catheters by retraction of the outer catheter away from the distal end of the inner catheter.

15. The device of claim 12 wherein the manifold further comprises:
  iii) a through lumen for permitting passage of a guide wire therethrough.

* * * * *